United States Patent [19]

Drent

[11] 4,311,862

[45] Jan. 19, 1982

[54] PREPARATION OF UNSATURATED ETHERS

[75] Inventor: Eit Drent, Amsterdam, Netherlands

[73] Assignee: Shell Oil Company, Houston, Tex.

[21] Appl. No.: 171,685

[22] Filed: Jul. 24, 1980

[30] Foreign Application Priority Data

Sep. 24, 1979 [GB] United Kingdom ............... 30595/79

[51] Int. Cl.$^3$ ............................................ C07C 41/06
[52] U.S. Cl. .................................................. 568/689
[58] Field of Search ...................................... 568/689

[56] References Cited

U.S. PATENT DOCUMENTS

| | | | |
|---|---|---|---|
| 2,922,822 | 1/1960 | Beach | 568/689 |
| 2,984,688 | 5/1961 | Sixt | 568/689 |
| 3,670,029 | 6/1972 | Romanelli | 568/689 X |
| 4,139,566 | 2/1979 | Kim et al. | 568/619 X |

FOREIGN PATENT DOCUMENTS

| | | | |
|---|---|---|---|
| 2550902 | 5/1977 | Fed. Rep. of Germany | 568/689 |
| 943160 | 11/1963 | United Kingdom | 568/689 |

*Primary Examiner*—Bernard Helfin

[57] ABSTRACT

Process for the preparation of olefinically unsaturated ethers by reacting a conjugated diene and a lower alkanol with the aid of an acidic catalyst in the presence of a non-basic aprotic polar solvent. The olefinically unsaturated ethers are of interest as solvents and gasoline additives and can also be used as starting materials for e.g. the synthesis of ketones.

14 Claims, No Drawings

PREPARATION OF UNSATURATED ETHERS

FIELD OF THE INVENTION

This invention relates to a process for the preparation of olefinically unsaturated ethers by reacting a conjugated diene and a lower alkanol using an acidic catalyst in the presence of a non-basic aprotic polar solvent.

BACKGROUND OF THE INVENTION

The present invention relates to a process for the preparation of olefinically unsaturated ethers from conjugated dienes and alkanols. The present invention relates in particular to a process for the preparation of butenylethers from butadiene and lower alkanols. The unsaturated ethers produced may be used as such, e.g. as solvents or as gasoline additives or may serve suitably as starting materials for chemical processes such as the conversion into the corresponding saturated ethers or into ketones.

It is known from U.S. Pat. No. 2,922,822 that alkenyl ethers can be produced by reacting conjugated dienes and lower alkanols in the presence of an acidic ion-exchange resin. Suitable reaction conditions comprise a large excess of alkanol which does not only serve as the reactant but also as the solvent. In the process for the preparation of butenyl-ethers from butadiene and lower alkanols as disclosed in German Offenlegungschrift No. 2,330,902 preference is given to a butadine/alkanol ratio of 1:2.

The above-mentioned processes however, suffer from the serious drawbacks that large amounts of unwanted by-products are formed under the reaction conditions. From Example 1 of German Offenlegungschrift No. 2,550,902 it appears that the butadiene-dimer 4-vinylcyclohexene (VCH) is even formed as the main product, thus wasting valuable starting material. In repeating the process described in U.S. Pat. No. 2,922,822 it was found that a substantial amount of low boiling dimethylether (DME), even as high as 51% based on methanol consumed, was found which renders the process on a large scale inadequate for the preparation of olefinically unsaturated ethers.

SUMMARY OF THE INVENTION

This invention is a process for preparing olefinically unsaturated ethers by reacting a conjugated diene and a lower alkanol using an acidic catalyst in the presence of a non-basic aprotic solvent. Using the process of this invention, the olefinically unsaturated ethers, and in particular butenylethers, can be prepared with high selectivities at relatively low temperatures. Not only is the amount of 4-vinyl cyclohexene produced virtually negligible, but also the amount of dimethylether produced is reduced considerably.

DESCRIPTION OF THE PREFERRED EMBODIMENTS

The present invention relates to a process for the preparation of olefinically unsaturated ethers by reacting a conjugated diene and a lower alkanol with the aid of an acidic catalyst which comprises carrying out the reaction in the presence of a non-basic aprotic polar solvent.

The expression "non-basic" refers to those aprotic polar solvents which do not possess a nitrogen atom capable of being protonated or an amine or amine precursor function such as an amide or a nitrile function.

Suitable conjugated dienes to be used in the process according to the present invention comprise $C_4$–$C_{12}$ conjugated dienes, especially $C_4$–$C_8$ conjugated dienes such as 1,3-butadiene, isoprene, cyclopentadiene, methylcyclopentadiene and 1,3-cyclohexadiene. Most preference is given to the use of 1,3-butadiene and isoprene.

Suitable lower alkanols to be used in the process according to the present invention comprise $C_1$–$C_4$ alkanols such as methanol, ethanol, n-propanol, isopropanol, n-butanol, sec-butanol and t-butanol. Most preference is given to the use of methanol and ethanol.

Suitable acidic catalysts to be used in the process according to the present invention comprise soluble acidic catalysts such as sulphuric acid, sulphonic acids, e.g. methane sulphonic acid or trifluoro methane sulphonic acid and trifluoro acetic acid as well as insoluble acidic catalysts, such as acidic ion-exchange resins. Preferred catalysts comprise the acidic ion-exchange resins such as acidic ion-exchange resins, i.e. those containing a plurality of sulphonic acid groups. Examples of such resins include sulphonated styrene-divinylbenzene copolymers, sulphonated phenol-formaldehyde resins, sulphonated benzene-formaldehyde resins and sulphonated perfluoropolyethers. The resin may be of the gel or the macroreticular type. The exchange capacity of the sulphonated resin is preferably at least 2.0 meq/g dry weight with exchange capacities in the range of from 3.0 to 5.5 meq/g dry weight being particularly preferred.

Specific examples of suitable resins include Amberlite IR 120 H, Amberlite A 252, Amberlite XE 307, Amberlyst 15 H, Dowex 50-X-4, Dowex MSC-14, Duolite C-20, Permutit QH, Chempro C-20, and Nafion. (Amberlite, Amberlyst, Dowex, Duolite, Permutit, Chempro and Nafion are registered Trade Marks).

The non-basic aprotic polar solvents suitable for use in the process according to the present invention include acyclic or cyclic sulphones, sulphoxides, ketones, (poly)ethers and nitromethane.

Suitable sulphones may be represented by the general formula:

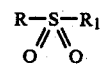

wherein R and $R_1$ represent the same or different aliphatic groups which may be joined together to form a cyclic sulphone.

Preferred acyclic sulphones are those according to the above formula wherein R and $R_1$ represent the same or different alkyl groups such as $C_1$ to $C_{12}$ alkyl groups. Specific examples includes dimethyl, diethyl, diisopropyl, dibutyl, methylethyl and methylbutylsulphones.

Preferred cyclic sulphones are sulpholane and alkylsulpholanes, such as those sulpholanes substituted by at least one $C_1$ to $C_8$ alkyl group. Specific examples include 2-methylsulpholane, 3-methylsulpholane, 3-butylsulpholane, 3-isopropylsulpholane and 2-methyl-4-butylsulpholane.

Suitable sulphoxides may be represented by the general formula:

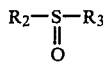

wherein $R_2$ and $R_3$, which may be the same or different represent, alkyl groups of up to 12 carbon atoms. Specific examples include dimethylsulphoxide and diethylsulphoxide.

Suitable ketones are those containing up to 8 carbon atoms in the molecule. Specific examples include dimethylketone, methylethylketone, methylpropylketone, methylisopropylketone and the various methylbutylketones. The use of methylethylketone is very convenient under the reaction conditions.

Suitable (poly)ethers comprise dialkylethers containing of from 4 to 12 carbon atoms in the molecule, cyclic ethers such as tetrahydrofuran, the dioxolanes and methyl-substituted dioxolanes, 1,3-dioxane and 1,4-dioxane and polyethers such as the mono- and dialkylethers of ethylene glycol and diethylene glycol. Preferred examples comprise the cellosolves such as methyl cellosolve and ethylcellosolve, the carbitols such as methyl carbitol, ethyl carbitol and butyl carbitol and the polyglymes such as the dimethyl and diethyl ethers of diethylene glycol or triethylene glycol. For practical purposes preference is given to the use of diglyme (the dimethyl ether of diethylene glycol).

The process according to the present invention is normally carried out using at least half the stoichiometric amount and preferably an excess of the conjugated diene in order to minimize the amount of coproduced dialkyl ether. Conjugated diene/alkanol molar ratios of up to 20:1 can be suitably applied, preference being given to a ratio in the range of from 1:1 to 6:1.

The amount of non-basic aprotic polar solvent to be applied in the process according to the present invention may vary between wide limits. Generally the amount of solvent to be used should be at least half the molar amount of alkanol used, preference being given to solvent/alkanol ratios in the range of from 1:2 to 10:1, ratios between 3:1 and 5:1 being particularly preferred. If desired mixtures of non-basic aprotic polar solvents can also be employed.

The process according to the present invention can be carried out batchwise, semi-continuously or continuously. For a batch process reaction times between 0.1 and 100 hours can be applied using the catalyst in an amount of from 1 to 25%, the remainder being the appropriate alkanol and non-basic aprotic polar solvent(s) in the range as indicated herein-above, the percentage based on the weight of the total reaction mixture including the non-basic aprotic polar solvent. For a continuous process using a solid catalyst, which is the preferred process, the total amount of non-basic aprotic polar solvent and the appropriate alkanol is suitably from 0.2 to 50 liters/kg catalyst (dry weight)/hour, amounts of from 1 to 25 liters/kg catalyst (dry weight)/hour being preferred. For such a continuous process the amount of conjugated diene is suitably from 0.05 to 10 kg/kg catalyst (dry weight)/hour, amounts of from 0.1 to 5 kg/kg catalyst (dry weight)/hour being preferred. For a continuous process using a soluble catalyst the concentration of the catalyst is suitably from 1 to 60% w based on the total reaction mixture including the non-basic aprotic polar solvent, and the amount of conjugated diene, and the total amount of non-basic aprotic polar solvent and the appropriate alkanol, are suitably from 0.02 to 10 kg/liter reactor volume/hour and from 0.05 to 50 liters/liter reation volume respectively.

The process according to the present invention is normally carried out at a rather mild temperature. Temperatures in the range of from 40° C. to 150° C. can be suitably applied. Very good results have been obtained using a non-basic aprotic polar solvent at a temperature in the range of from 70° C. to 100° C. The amount of dialkylether produced decreases substantially when the reaction is carried out at a lower temperature.

The process according to the present invention can be carried out at autogenous pressure but is preferably carried out at a pressure which maintains the non-basic aprotic polar solvent and the alkanol in the liquid state. Suitable reaction pressures are from 1 to 200 bars. Very good results were achieved using pressures between 20 and 60 bars.

The process according to the present invention is of great interest for the preparation of alkylbutenyl ethers from butadiene and lower alkanols, in particular for the preparation of the methyl butenyl ethers from butadiene and methanol. Under the prevailing reaction conditions the secondary methyl butenyl ether is formed in slightly higher amounts than the primary methyl butenyl ether. The ratio between the secondary and the primary ether can be adjusted to some extent by varying the process conditions.

It should be noted that conjugated dienes in admixture with non-conjugated dienes, and/or mono-olefinically unsaturated compounds and/or non-olefinic compounds, e.g. alkanes, can be suitably used as a feedstock for the process according to the present invention.

For instance, use can be made from so-called BBB fractions, which are normally available from naphtha crackers, comprising butadiene and a mixture of isomeric butenes with isomeric butanes. Such mixtures, whether fresh feedstock or (partly) recycle mixtures, may be contacted with a non-basic aprotic polar solvent which causes separation of the butadiene from the butene(s)/butane(s) which can be effected by e.g. extractive distillation. The bottom product comprising mainly butadiene/non-basic aprotic polar solvent can conveniently be used as the starting material for the preparation of the alkyl butenyl ethers according to the process according to the present invention.

When the process according to the present invention is carried out continuously, a conjugated diene (e.g. liquid butadiene, if desired obtained from a BBB fraction as indicated hereinabove) and a mixture of the appropriate alkanol and the non-basic aprotic polar solvent are fed into a reactor containing a solid acidic ion-exchange resin. If desired the conjugated diene and the alkanol/non-basic aprotic polar solvent may be premixed. After the reaction which is preferably carried out under pressure to keep the reactants and the products in the liquid phase, the reaction mixture may be worked up by any convenient technique.

Suitably, unconverted butadiene can be removed by distillation and can be (partly) recycled to the reactor. The non-basic aprotic polar solvent will normally be obtained as the bottom fraction of a further distillation column and can be recycled. If desired a further separation of the methyl butenyl ethers can be achieved by distillation. The yield ratio of the ethers can be adjusted by (partially) recycling one of the two isomers.

The use of sulpholane is of special interest in that this compound can be used as the non-basic aprotic polar solvent to be used in the process according to the present invention and can also be used for extracting butadiene form BBB fractions. This avoids the necessity of a solvent switch in such a combined process.

An alternative procedure starting from a butadiene/isobutene containing feedstock, for example a BBB feedstock containing also n-butenes and butanes, for the preparation of olefinically unsaturated ethers from conjugated dienes and alkanols comprises firstly treating the feedstock in the presence of an acidic catalyst, preferably an acidic ion-exchange resin with a lower alkanol, preferably with methanol, to produce an alkyl t-butyl ether (methyl t-butyl ether starting from methanol) which compound can be of interest as such, followed by contacting the isobutene-depleted fraction with the non-basic aprotic polar solvent, preferably sulpholane which will cause extraction of butadiene. The butadiene-rich extract thus obtained can be converted with the aid of an acidic catalyst into the alkyl butenyl ethers (which can be decomposed into butadiene and the lower alkanol) as described hereinbefore.

The invention will be illustrated by reference to the following Examples which are provided for illustration and are not to be construed as limiting the invention.

EXAMPLE 1

Preparation of methylbutenyl ethers

A reaction column (30×1 cm) was packed with 9.5 g dry weight of a sulphonated styrene-divinylbenzene macroporous cation exchange resin in the hydrogen form (Amberlite 252 H+) which had previously been dried for 20 hours at 100° C. at reduced pressure. The various non-basic aprotic polar solvent/methanol mixtures employed (80:20 weight ratio) were rigorously dried by refluxing for several hours over molecular sieves. Before entering the reaction column the liquid was mixed with liquid butadiene and passed over a pre-bed of activated molecular sieves at ambient temperature to remove the last traces of water so as not to impair the catalytic activity. The reactions were carried out at 85° C. or at 120° C. at a pressure sufficient to keep the reactants and products in the liquid phase. The reaction effluent was cooled, collected under a pressure of about 2 atmospheres and analysed by means of gas-liquid chromatography. The specific reaction conditions and the results obtained are given in Table 1. It will be clear that the presence of a non-basic aprotic polar solvent not only improves considerably the selectivity to the methyl butenyl ethers but also shows a much higher catalyst activity (compare experiments I–IV, especially Experiment III with the comparative experiments a and b).

EXAMPLE 2

Preparation of methyl butenyl ethers

The experiments described in Example 1 were repeated but at a pressure of 15 bar and using either no non-basic aprotic polar solvent (comparative experiments c and d using excess methanol and comparative experiment using the non-basic aprotic non-polar solvent toluene) or sulpholane in various ratios (experiments V and VI). The specific conditions and results are given in Table 2.

TABLE 1

|  | a | b | I | II | III | IV |
|---|---|---|---|---|---|---|
| Solvent | none | none | methyl ethyl ketone | diglyme | sulpholane | sulpholane |
| Pressure (bar) | 30 | 30 | 30 | 30 | 30 | 30 |
| Temperature (°C.) | 120 | 85 | 85 | 85 | 85 | 85 |
| Liquid Hourly Space Velocity (1 . kg$^{-1}$ . h$^{-1}$)* | 4.2 | 4.2 | 4.2 | 4.2 | 4.2 | 4.2 |
| Butadiene Space Velocity (Kg . kg$^{-1}$ . h$^{-1}$) | 1.3 | 1.3 | 1.3 | 1.3 | 1.3 | 0.63 |
| Methanol conversion (%) | 41 | 3.5 | 18 | 24 | 33 | 45 |
| Selectivity to methyl butenyl ethers (%)** | 49 | 59 | 79 | 86 | 92 | 84 |
| Selectivity to DME (%)** | 51 | 41 | 21 | 14 | 8 | 16 |
| Butadiene conversion (%) | 49 | 5.3 | 7.5 | 12 | 19 | 26 |
| Selectivity to methyl butenyl ethers (%)*** | 99 | 99 | 99 | 99 | 99 | 99 |
| Selectivity to VCH (%)*** | 1 | 1 | 1 | 1 | 1 | 1 |
| Space time yield of methyl butenyl ethers (kg . kg$^{-1}$ . h$^{-1}$) | 0.98 | 0.10 | 0.14 | 0.24 | 0.38 | 0.27 |

*liquid refers to methanol or methanol/non-basic aprotic polar solvent mixture
**based on methanol consumed
***based on butadiene consumed

TABLE 2

|  | c | d | e | V | VI |
|---|---|---|---|---|---|
| Solvent | none | none | toluene | sulpholane | sulpholane |
| Temperature (°C.) | 100 | 120 | 100 | 80 | 80 |
| Weight Hourly Space Velocity (kg . kg$^{-1}$ . h$^{-1}$) | 4.5 | 4.5 | 4.2 | 3.5 | 3.5 |
| Butadiene/methanol/solvent ratio (100% w) | 10/90 | 10/90 | 23/7/70 | 30/12/58 | 30/24/46 |
| Butadiene conversion (% m) | 14 | 50 | 16 | 40 | 25 |

TABLE 2-continued

| | c | d | e | V | VI |
|---|---|---|---|---|---|
| Selectivity to methyl butenyl ethers* | — | 30 | 35 | 98 | 98 |
| Space time yield of 3-methoxy butene-1 (kg . kg$^{-1}$ . h$^{-1}$) | 0.06 | 0.23 | 0.1 | 0.4 | 0.24 |
| Space time yield of 1-methoxy butene-2 (kg . kg$^{-1}$ . h$^{-1}$) | 0.03 | 0.16 | 0.07 | 0.3 | 0.16 |

*based on methanol consumed

EXAMPLE 3

Coproduction of methyl butenyl ethers and methyl t-butyl ether

The experiments described in Example 2 were repeated but using a BBB feedstock composition comprising butadiene (43% w), isobutene (26% w) inbutenes (27% w) and butanes (4% w). The reaction temperature was 80° C. and a BBB/methanol/sulpholane composition (10/20/70) was passed over the catalyst at a liquid hourly space velocity of 4.5 kg.kg$^{-1}$.h$^{-1}$. The conversion of butadiene was 20% m and that of isobutene 98% m. The space time yield of the methyl butenyl ethers was 0.07 kg.kg$^{-1}$.h$^{-1}$ and the space time yield of methyl t-butyl ether (from isobutene) was 0.2 kg.kg$^{-1}$.h$^{-1}$. This experiment clearly demonstrates that not only n-butenes and butanes can be present in the butadiene feedstock for the preparation of methyl butenyl ethers but also that methyl t-butyl ether is formed in high yield from isobutene whilst the methyl butenyl ethers are already coproduced in reasonable amounts.

An experiment carried out at 60° C. using an 84/16 BBB/methanol feedstock in the absence of sulpholane showed that under the reaction conditions virtually no butadiene is converted (<1%) whereas isobutene is converted (95%) into methyl t-butyl ethers indicating that no undesirable side reactions occur which consume butadiene under reaction conditions favorable to the production of methyl t-butyl ether.

What is claimed is:

1. A process for the preparation of olefinically unsaturated ethers by reacting a C$_4$–C$_{12}$ conjugated diene with a C$_1$–C$_8$ alkanol by contacting said diene with said alkanol with an acid catalyst selected from the group consisting of sulfuric acid, a sulphonic acid, trifluoroacetic acid and a sulphonic acid ion-exchange resin at a temperature of from about 40° C. to about 150° C. and a pressure of from about 1 to about 200 bars in the presence of a non-basic aprotic solvent selected from the group consisting of a cyclic sulphone, an acyclic sulphone, a sulphoxide, a ketone, a (poly)ether and a nitromethane, wherein the molar ratio of conjugated diene/alkanol ranges from about 1:1 to about 6:1, the amount of solvent/alkanol used ranges from about 1:2 to about 10:1.

2. The process of claim 1 wherein the conjugated diene is a C$_4$–C$_8$ diene and the alkanol is a C$_1$–C$_4$ alkanol.

3. The process of claim 2 wherein the alkanol is methanol or ethanol.

4. The process of claim 1 wherein the catalyst is a sulphonated styrene-divinyl benzene copolymer.

5. The process of claim 1 wherein the solvent is a sulphone which is represented by the formula:

wherein R and R$_1$ represent the same or different aliphatic groups which may be joined together to form a cyclic sulphone.

6. The process of claim 5 wherein the sulphone is a cyclic sulphone.

7. The process of claim 6 wherein the sulphone is sulpholane or alkyl-sulpholane.

8. The process of claim 1 wherein the solvent is a ketone which contains up to 8 carbon atoms.

9. The process of claim 8 wherein the ketone is methyl ethyl ketone.

10. The process of claim 1 wherein the solvent is a (poly)ether which is a mono-or dialkylether of ethylene glycol or diethylene glycol.

11. The process of claim 10 wherein the polyether is the dimethyl ether of ethylene glycol.

12. The process of claim 1 wherein the amount of solvent/alkanol used ranges from about 3:1 to about 5:1.

13. The process of claim 1 wherein the reaction temperature ranges from about 70° C. to about 100° C.

14. The process of claim 1 wherein the pressure ranges from about 20 to about 60 bars.

* * * * *